United States Patent
Singh

(10) Patent No.: US 11,992,571 B2
(45) Date of Patent: May 28, 2024

(54) PENS/PENCILS SANITIZING MACHINE

(71) Applicant: Shashwat Singh, Frisco, TX (US)

(72) Inventor: Shashwat Singh, Frisco, TX (US)

( * ) Notice: Subject to any disclaimer, the term of this patent is extended or adjusted under 35 U.S.C. 154(b) by 295 days.

(21) Appl. No.: 17/328,017

(22) Filed: May 24, 2021

(65) Prior Publication Data
US 2022/0096688 A1   Mar. 31, 2022

Related U.S. Application Data

(60) Provisional application No. 63/085,378, filed on Sep. 30, 2020.

(51) Int. Cl.
*A61L 2/22*   (2006.01)
*A61L 2/26*   (2006.01)
*B43M 99/00*   (2010.01)

(52) U.S. Cl.
CPC .......... *A61L 2/22* (2013.01); *A61L 2/26* (2013.01); *A61L 2202/15* (2013.01); *B43M 99/008* (2013.01)

(58) Field of Classification Search
None
See application file for complete search history.

(56) References Cited

FOREIGN PATENT DOCUMENTS

| CN | 206391232 U | * | 8/2017 |
| DE | 102015120295 B3 | * | 2/2017 |
| TW | M414878 U1 | * | 11/2011 |

OTHER PUBLICATIONS

Chen, B. TWM414878U1—translated document (Year: 2011).*
Hsu, W. DE 102015120295B3—translated document (Year: 2015).*
Dai et al. CN206391232U—translated document (Year: 2017).*

* cited by examiner

*Primary Examiner* — Jelitza M Perez

(57) ABSTRACT

Coronavirus disease (COVID-19) is an infectious disease caused by a newly discovered coronavirus. COVID-19 is affecting the whole world and it's not only taking lives but also heavily penalizing the economy. This new invention 'Novel Pens/Pencils Sanitizing Machine' helps in reducing the risks of getting COVID-19 and other common infectious diseases like Flu, common cold etc. through the use of common pens and pencils. Many facilities front desk like schools, doctor's offices, Hospitals, private offices share the same pens or pencils with others or sanitizes the pens or pencils manually which is a time taking and tedious job. This machine sanitizes bunch of pens and pencils in one go in an automated way.

1 Claim, 3 Drawing Sheets

PENS/PENCILS SANITIZING MACHINE

BACKGROUND

COVID-19 has spread to almost every country in the world and we have taken bunch of precautions to slow down its spread. We sanitize many things but often in school or colleges or offices we use the same pen or pencil to sign the form or check-in to the Doctor's offices or hospitals or Real estate deals or any place where manual signature is required. Currently we have the various sanitizers available in the market but none of them is designed or created to sanitize the pens and pencils in an automated way. COVID-19 or other infectious diseases like Flu or common cold might spread through the use of same pen or pencils by many people. One of the solution is to sanitize each pen or pencils manually after each use which is a tedious job. Therefore a need exists for a novel Pens/Pencils sanitizing machine. This invention can sanitize bunch of pens or pencils in one go in an automated fashion.

BRIEF SUMMARY OF THE INVENTION

The present invention comprises of a platform with a slow rotating plate. The rotating plate holds the pen or pencil holder. The top of the frame would have a sanitizer unit which would blow the mist towards the pens or pencils holder. Pens or pencils get sanitized by the mist. Slow rotation will ensure that every pen or pencil gets the sanitizing mist. The rotation of plate and sanitizer mist can be triggered using the sensor or with a push of a button.

DETAILED DESCRIPTION OF THE INVENTION

Reference will now be made in detail to certain embodiments of the invention, examples of which are illustrated in the accompanying drawings. While the invention will be described in reference to these figures and certain implementations and examples of the embodiments, it will be understood that such implementations and examples are not intended to limit the invention. To the contrary, the invention is intended to cover alternatives, modifications, and equivalents that are included within the spirit and scope of the invention as defined by the claims. In the following disclosure, specific details are given to provide a thorough understanding of the invention. References to various features of this "invention" throughout this document do not mean that all claimed embodiments or methods must include the referenced features. It will be apparent to one skilled in the art that the present invention may be practiced without these specific details or features.

This invention is able to sanitize bunch of pens and pencils in one go with the help of disinfecting mist and rotating plate.

Figure 1:
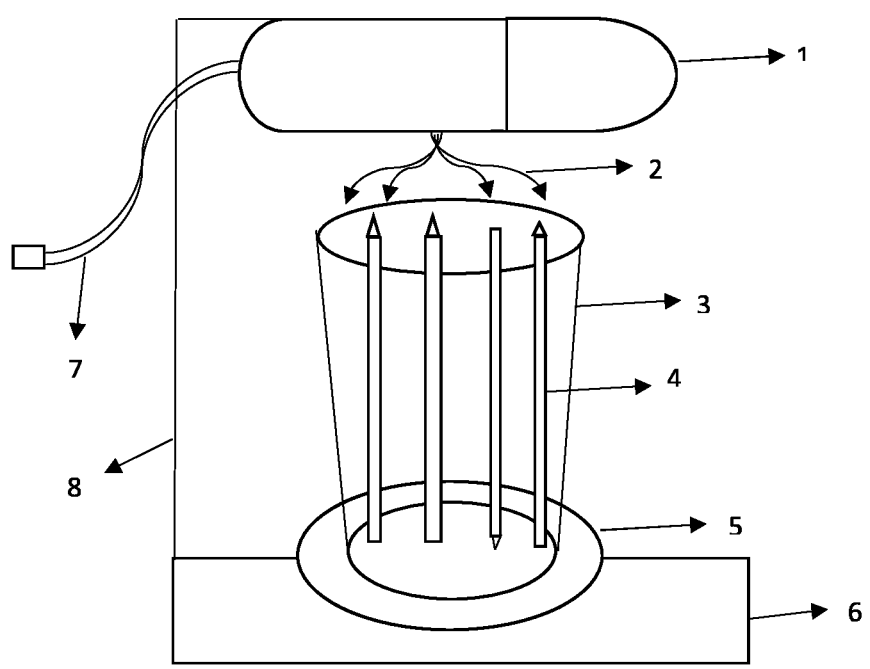

FIG. 1 presents the front view of the machine where number 1 in figure represents sanitizing unit which sprays the mist. The bottom of the container from where the mist is coming from has a mist plate which is attached to mist circuit which turns on by connecting to USB port or battery and produces the mist. Mist plate is firmly attached to the container at the bottom. The bottom of the container should have a hole so that liquid keeps going to plate, which in turn would make the mist, which goes to pens and pencils.

Figure 2:
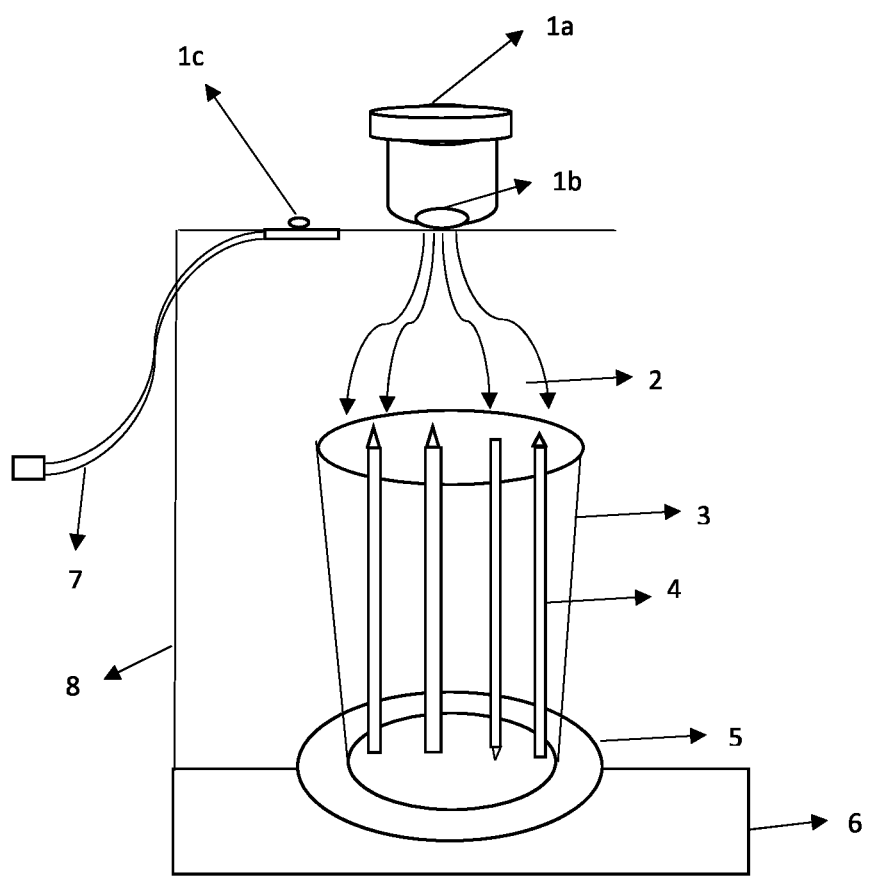

FIG. 2 presents the front view of the machine with an alternate design where number 1a represents container holding the sanitizing liquids. 1b represents the mist plate which is attached to the container at the bottom. FIG. 2, 1c represents mist circuit which is attached to the rectangular rod under the bottom part with on and off switch. The on and off switch helps to turn on or off the mist. The mist circuit is attached to the bottom of the mist plate by an electrical wire.

FIG. 1, 2 represents the mist going to the box containing the pens and pencils. Mist is shown by the arrow. During the run time the mist can be seen inside the pen and pencil box as box has a depth and is covered by the sides which holds the mist.

FIG. 1, 3 represents a pen or pencil holder. The holder can hold a bunch of pens and pencils.

FIG. 1, 4 represents pens or pencils.

FIG. 1, 5 represents rotating plate. This rotating plate is attached to a slow running motor shaft by a pin on both sides and sits on the top of the bearing plate so that smooth rotation happens.

FIG. 1, 6 represents the structure holding the mist container which is a self-standing structure. It has either a single rectangular shaped rod pillar or two rectangular shaped rod pillars, which rest on a rectangular, circular or oval base. The upper surface of the rod holds the sanitizing liquids containers and the bottom of the rod contains the mist circuit and an on and off switch. The lower surface of rod can also hold the sanitizing liquid container.

FIG. 1, 7 represents the wire with connector at the end to charge the mist producing unit.

FIG. 1, 8 represents a rectangular shaped rod which is attached to the base and the upper surface of the rod holds the sanitizing liquids containers and the bottom of the rod contains the mist circuit and an on and off switch.

To sanitize the pens and pencils the following steps should be performed:—

Step 1: Put enough pens and pencils in the holder so that these don't lie on each other. Based on need the box size can be increased and accordingly the size of the sanitizing liquid mist makers.

Step 2: Connect the slow running motor to a power outlet.

Step 3: Place the holder on the base and the holder should have the pens that need to be sanitized.

Step 4: The pen/pencil holder will start rotating. This will ensure all pens and pencils expose to the disinfectant mist.

Step 5: Turn on the mists, ensure mist starts going towards the pens and pencils. Run time of the mist should be as per sanitizing liquid specifications. Mist should be run for the period of time recommended by the sanitizing liquid specification to kill the viruses. Once done, the mist should be turned off.

Step 6: Remove the holder holding the pens.

Step 7: Place another holder if you want to sanitize more pens or else turn off the mist and disconnect the motor from the power outlet.

BRIEF DESCRIPTIONS OF THE DRAWINGS

FIG. 1 presents the front view which has all components working in harmony. Details of each sub-component is given below:—

1 represents the sanitizing units holding the sanitizing liquids. The bottom of the container from where the mist is coming has a mist plate which turns on by connecting to USB port or battery and produces the mist. Mist plate is firmly attached to the container at the bottom.

2 represents mist coming out from the container.

- 3 represents pen or pencil holder. The holder can hold bunch of pens and pencils.
- 4 represents pens or pencils.
- 5 represents rotating plate.
- 6 represents the structure holding the mist container which is self-standing structure. It has single pillar which rest on a square, circular or oval base. The top end of pillar is connected by a rectangular shaped rod. The upper surface of rod holds the sanitizing liquids containers and the bottom of the rod contains the mist circuit and an on and off switch. The lower surface of rod can also hold the sanitizing liquid container.
- 7 represents a wire to either charge the mist unit or to supply the power to mist unit directly.
- 8 represents a rectangular shaped rod which is attached to the base and the upper surface of rod holds the sanitizing liquids containers and the bottom of the rod contains the mist circuit and an on and off switch.

FIG. 2 which is front view represents the alternative design of the same product.

- 1a represents mist sprayer container which contains the sanitizing liquid.
- 1b represents mist sprayer plate which is attached to sanitizing liquid container base.
- 1c represents mist circuit with on and off switch which is attached to mist sprayer plate by wire.
- 2-8 represents the exact same components from FIG. 1

Figure 3:
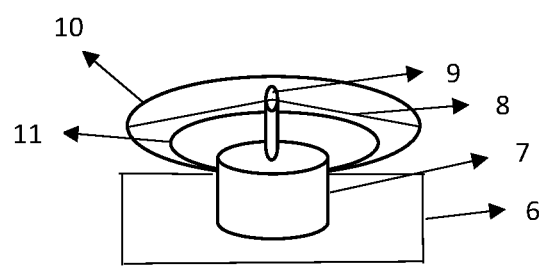

FIG. 3 depicts rotating plate components from front view. Details of each sub-component is given below:—

- 6 represents the frame to which slow running motor is attached.
- 7 represents the slow running motor with shaft.
- 8 represents the pin which attaches the rotating plate to the motor shaft so that on shaft rotation the plates rotates too.
- 9 represents the motor shaft to which the pin is attached which in turn is attached to rotating plate.
- 10 represents an outer rotating plate on which the pens or pencils holder is placed.
- 11 represents the bearing plate which rests on motor body and the outer rotating plate rests on this bearing plate. The bearing plate helps outer plate to rotate smoothly on motor shaft rotation.

Some embodiments of the present invention are illustrated as an example and are not limited by the figures of the accompanying drawings.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

What is claimed is:

1. A Pens/Pencils Sanitizing Machine which sanitizes a bunch of pens or pencils in one go, comprising: a sanitizing unit having a frame which has a rectangular or circular or oval shape base with one or two rectangular shaped rod pillars which holds a container with sanitizing liquids; the container being attached either underneath or at the top of the rectangular rod; a mist making plate attached to the bottom of the container to create the mist; a mist circuit attached to the bottom of the rectangular rod outside of the container with an on and off switch to turn on or off the mist, a rotating plate; a slow rotating motor with a shaft which is connected to the rotating plate by a pin on both sides; a bearing plate sitting on a motor body; and a circular or oval shaped plate which is attached to the shaft and rests on the bearing plate for smooth rotations.

\* \* \* \* \*